(12) United States Patent
Aflatoon

(10) Patent No.: US 8,915,963 B2
(45) Date of Patent: Dec. 23, 2014

(54) ARTIFICIAL DISC PROSTHESIS FOR REPLACING A DAMAGED NUCLEUS

(76) Inventor: Kamran Aflatoon, Corona del Mar, CA (US)

( * ) Notice: Subject to any disclaimer, the term of this patent is extended or adjusted under 35 U.S.C. 154(b) by 46 days.

(21) Appl. No.: 13/288,132

(22) Filed: Nov. 3, 2011

(65) Prior Publication Data

US 2012/0116516 A1 May 10, 2012

Related U.S. Application Data

(63) Continuation-in-part of application No. 12/384,095, filed on Mar. 31, 2009, now Pat. No. 8,147,555.

(60) Provisional application No. 61/072,480, filed on Mar. 31, 2008.

(51) Int. Cl.
*A61F 2/44* (2006.01)
*A61F 2/30* (2006.01)

(52) U.S. Cl.
CPC ......... *A61F 2/442* (2013.01); *A61F 2230/0065* (2013.01); *A61F 2002/444* (2013.01); *A61F 2002/30224* (2013.01); *A61F 2002/30601* (2013.01); *A61F 2250/0018* (2013.01); *A61F 2002/30291* (2013.01); *A61F 2220/0025* (2013.01); *A61F 2002/30261* (2013.01); *A61F 2220/0033* (2013.01); *A61F 2002/30841* (2013.01); *A61F 2002/30014* (2013.01); *A61F 2002/30372* (2013.01); *A61F 2230/0091* (2013.01); *A61F 2230/0069* (2013.01); *A61F 2002/30579* (2013.01); *A61F 2002/302* (2013.01); *A61F 2002/30586* (2013.01); *A61F 2002/30578* (2013.01); *A61F 2002/30528* (2013.01); *A61F 2002/30584* (2013.01); *A61F 2002/30884* (2013.01); *A61F 2/441* (2013.01); *A61F 2002/30563* (2013.01)

USPC .................. 623/17.15; 623/17.16; 623/17.11

(58) Field of Classification Search
USPC .......... 623/11.11, 17.11, 17.12, 17.13, 17.15, 623/17.16
See application file for complete search history.

(56) References Cited

U.S. PATENT DOCUMENTS

| | | | | |
|---|---|---|---|---|
| 4,309,777 | A * | 1/1982 | Patil ............................ | 623/17.13 |
| 4,874,389 | A * | 10/1989 | Downey ...................... | 623/17.16 |
| 5,062,850 | A * | 11/1991 | MacMillan et al. ........ | 623/17.11 |
| 5,071,437 | A * | 12/1991 | Steffee, Arthur D. ...... | 623/17.16 |
| 5,133,762 | A * | 7/1992 | Branemark ................. | 623/21.12 |
| 2003/0195628 | A1 * | 10/2003 | Bao et al. ................... | 623/17.12 |
| 2005/0015152 | A1 * | 1/2005 | Sweeney .................... | 623/17.14 |
| 2008/0077242 | A1 * | 3/2008 | Reo et al. ................... | 623/17.15 |

* cited by examiner

*Primary Examiner* — David Bates
*Assistant Examiner* — Samuel Hanna
(74) *Attorney, Agent, or Firm* — Ober, Kaler, Grimes & Shriver; Royal W. Craig; Christopher F. Lonegro

(57) ABSTRACT

A multi-piece disc replacement implant for replacing a disc removed by a discectomy including an upper plate member, a lower plate member, and an intermediate resilient member providing movement between the two plate members replicating the natural movement of the spine. The plate members are rigid and have orthogonal sidewalls forming an enclosure. The resilient member is an elastic solid or a multi-chamber balloon structure of fluid-filled sacks that collectively define a non-uniform shape such as an oblate spheroid, or a helically coiled string of beads. Such an implant is capable of supporting the compressive and cyclic loads required of a natural disc. The upper and lower plate members are cooperatively formed to selectively limit the allowable range of motion in any given direction and a provided with protrusions to be received in one or more channels cooperatively formed in the vertebrae and secured in place by a bone screw.

12 Claims, 9 Drawing Sheets

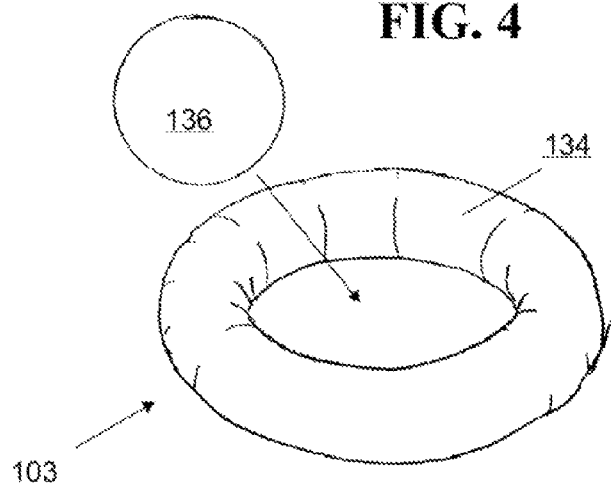
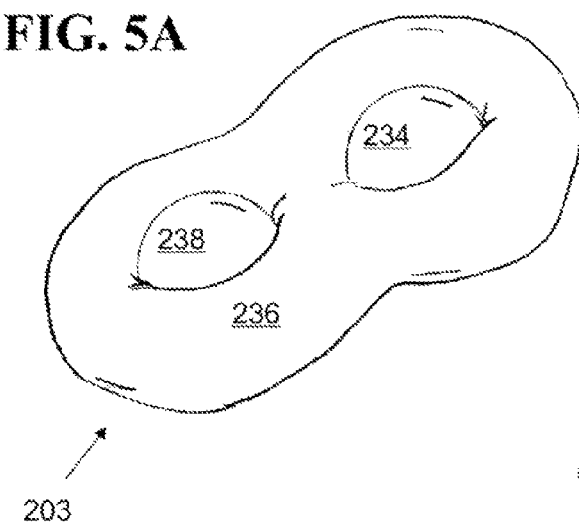
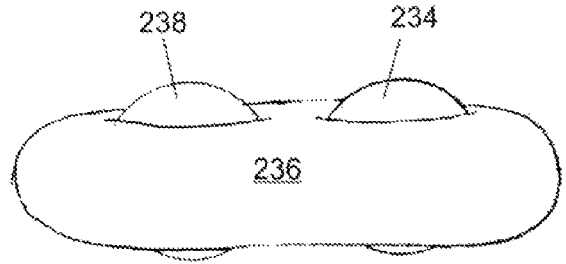

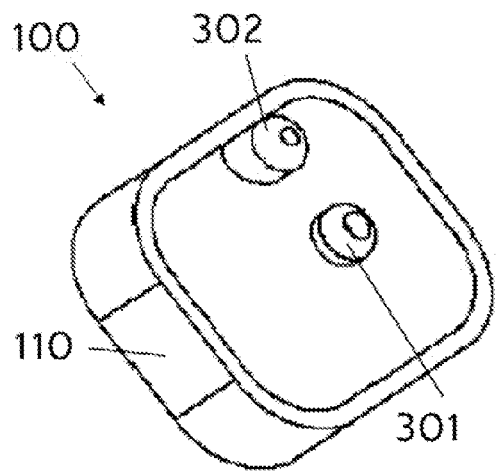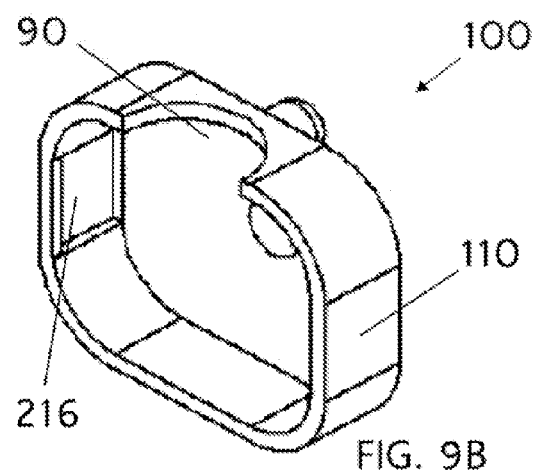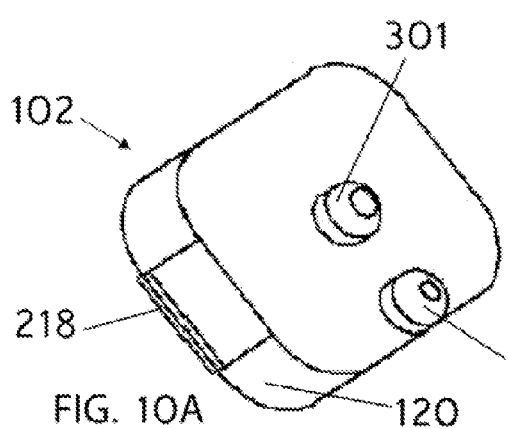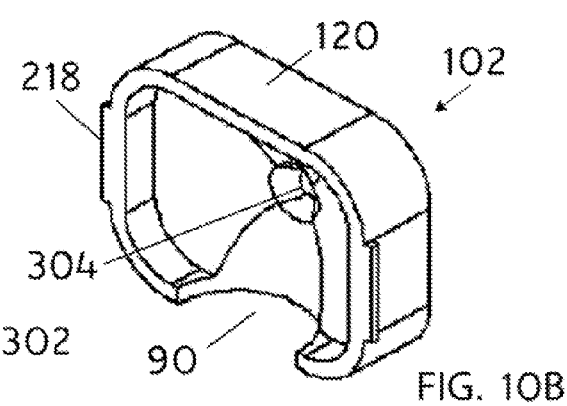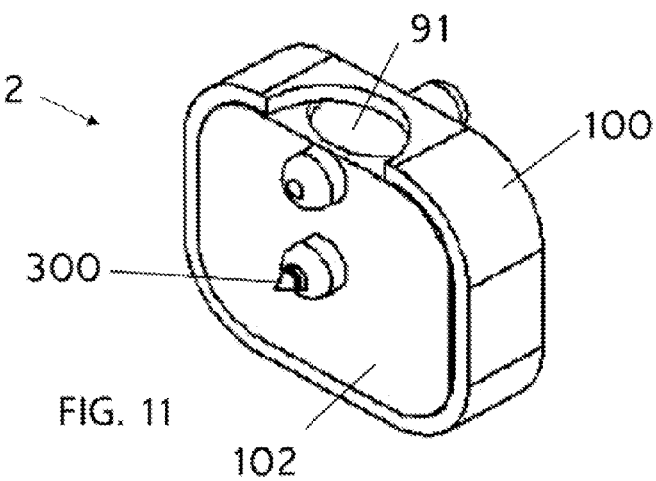

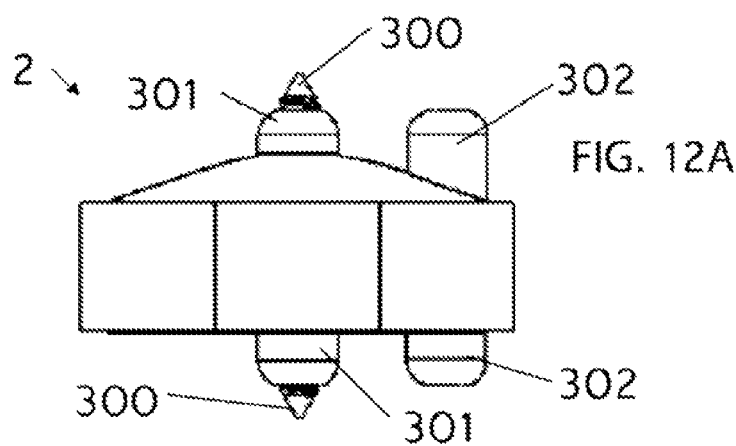
FIG. 12A
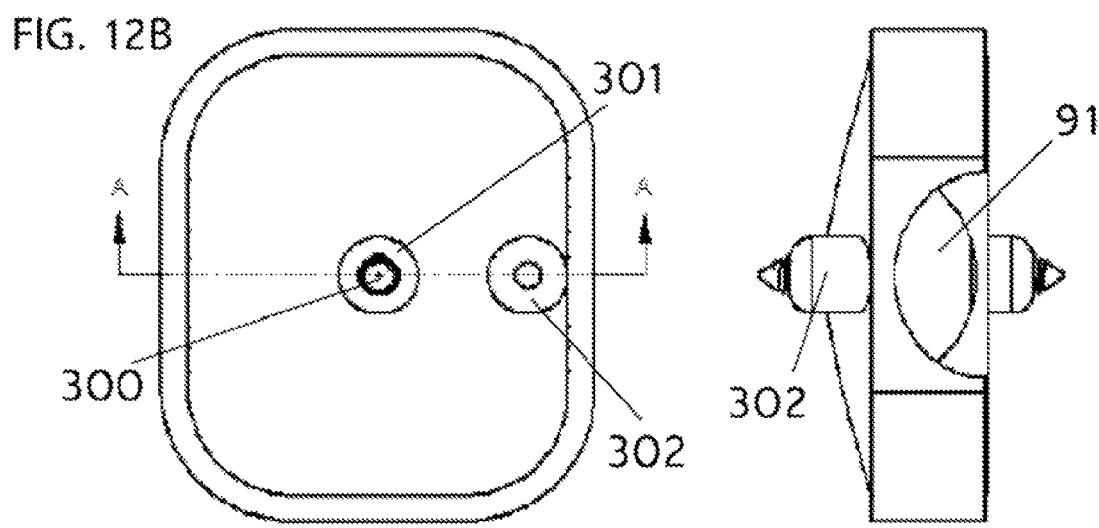
FIG. 12B
FIG. 12D
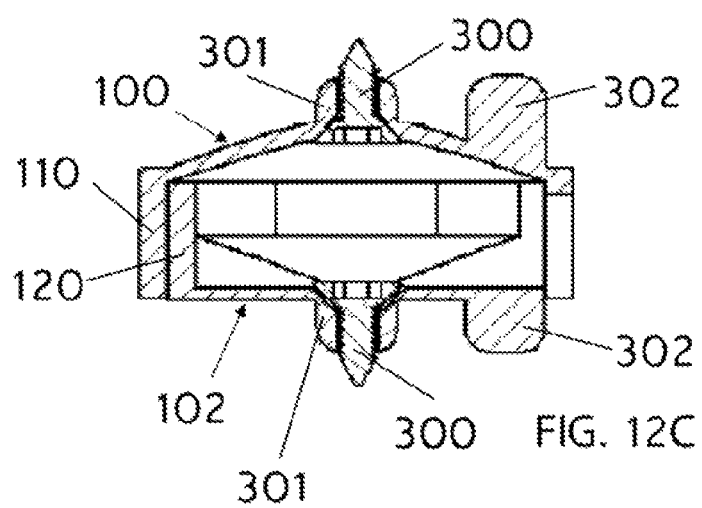
FIG. 12C

ARTIFICIAL DISC PROSTHESIS FOR REPLACING A DAMAGED NUCLEUS

CROSS-REFERENCE TO RELATED APPLICATIONS

The present application is a continuation in part of U.S. patent application Ser. No. 12/384,095 filed Mar. 31, 2009 now U.S. Pat. No. 8,147,555 which is incorporated herein by reference and which claims priority from provisional application 61/072,480 filed on Mar. 31, 2008 which is also incorporated herein by reference.

BACKGROUND OF THE INVENTION

1. Field of the Invention

The present invention relates to artificial intervertebral disc implants and, in particular, to a multi-chamber balloon implant that inflates to create an oblate spheroid shape.

2. Description of the Background

Intervertebral discs are oblate spherical structures (visibly flattened at the poles and bulging at the equator) that maintain the space between adjacent vertebrae and function as a cushion by absorbing and mitigating forces acting on the spine as a result of daily activities. Each intervertebral disc consists of an outer annulus fibrosus, which surrounds the inner nucleus pulposus. The annulus fibrosus consists of several layers of strong annular fibrocartilage to contain the nucleus pulposus and distribute pressure evenly across the disc. The nucleus pulposus contains loose fibers suspended in a mucoprotein gel that serves to absorb shocks and maintain the intervertebral space as the vertebra move relative to one another.

Deterioration of an intervertebral disc can result from disease, trauma or aging, and results in symptoms including limited mobility, and severe pain. As a result of normal aging the nucleus pulposus loses its ability to retain fluid and contracts in volume resulting in a reduction in the intervertebral space. This reduction may put pressure on the nerves of the spinal column causing pain. Reduction in volume of the nucleus pulposus also reduces the disc's ability to absorb shock which, coupled with age or trauma related weakening of the annulus fibrosus often results in a disc herniation. When the annulus fibrosus tears due to an injury or the aging process, the nucleus pulposus can begin to extrude through the tear. This is called disc herniation, a prolapsed disc or, more colloquially, a slipped or ruptured disc. The bulge of a herniated disc may also put pressure on nearby nerve structures resulting in radiating pain, numbness, tingling, and diminished strength and/or range of motion. In addition, the nucleus pulposus contains proteins which, if extruded from the disc into contact with the neural structures may also cause inflammation and significant pain.

The majority of minor herniated discs will on their own without surgical intervention. Physical therapy and pharmaceutical interventions are often sufficient to manage the condition until this healing can occur. Non-steroidal anti-inflammatory medications are commonly prescribed as are epidural steroid (cortisone) injections, both in conjunction with weight loss and rehabilatory exercise programs. Traditional pain management approaches are also applied. In a significant number of patients surgical intervention is required when these non-invasive techniques are unsuccessful.

A wide variety of surgical options are available including laminectomy and discectomy combined with vertebral fusion and/or dynamic stabilization. However, these surgical options are highly invasive and require prolonged hospitalization and recovery. More recently, artificial disc replacement prosthetics have been used to replace or augment all or part of the removed or resected intervertebral disc. Some such prosthetics use a ball and socket arrangement. For example, U.S. patent application Ser. No. 10/997,823 for "Articulating Spinal Disc Prosthetic" by the inventor herein et al. shows a disc prosthetic including a superior (upper) plate, inferior (lower) plate, and intermediate layer, in a sandwich. The intermediate member is sandwiched between the superior and inferior plate members with conforming sides, and includes a short cylindrical post protruding downward into a circular recess in the inferior plate member to center it and to maintain a predetermined spacing there between. The post includes snap-in spring fingers that lock into the recess of the inferior member to prevent withdrawal.

There are also a variety of spring discs that employ springs sandwiched between metal endplates. For example, U.S. Pat. No. 5,458,642 to Beer et al. issued Oct. 17, 1995 shows a synthetic intervertebral disc for implantation in the human body. The disc is comprised of disc-shaped plates 11 joined by springs along the inside. The spring system distributes forces acting on the disc between the springs and allows normal movement of the vertebrae during flexion and extension of the spine in any direction.

Still other disc prosthetics are soft cushions with material properties more similar to the discs that they replace. Examples of such disc replacements are disclosed in U.S. Pat. Nos. 5,702,450 and 5,035,716, which employ elastic cushion "formed of a disk material with mechanical properties as similar as possible to the properties of a natural disk."

The general concept of an expandable balloon-like artificial disc prosthesis filled with a polymer such as silicone is well known. Some of these fixate externally to the vertebrae. For example, United States Patent Application 20060085074 by Raiszadeh, Kamshad published Apr. 20, 2006 shows an expandable intradiscal prosthetic configured to be placed between two vertebrae.

United States Patent Application 20070250169 by Lang, Philipp published Oct. 25, 2007 shows a joint arthroplasty device formed in situ by inserting a hollow device having an aperture and a lumen into a target joint, and injecting material into the hollow device to form an implant.

United States Patent Application 20070135922 by Trieu, Hai H. published Jun. 14, 2007 and his issued U.S. Pat. No. 7,182,783 issued Feb. 27, 2007 both show selectively expandable composite structures useful as spinal arthroplasty devices. The structures comprise an outer shell comprised of a non-hydrogel polymer material. At least one core is positioned within the outer shell and this may be comprised of a hydrophilic polymer. The core expands upon hydration, thereby deforming the outer shell.

United States Patent Application 20070073290 by Boehm, Frank H. JR. published Mar. 29, 2007 shows an artificial/prosthetic facet joint with ballotable/compressible joint space component composed of latex, polymer, silicone, or any other substance either previously used in the art or not. This flexible outer surface contains within it, a ballottable fluid or gelatinous center.

United States Patent Application 20060241759 by Trieu, Hai H. (SDGI) published Oct. 26, 2006 shows oriented polymeric spinal implants wherein the polymer material is substantially uniformly oriented for increased strength perpendicular to the orientation of the polymer material.

United States Patent Application 20060206209 by Cragg et al. published Sep. 14, 2006 shows a prosthetic nucleus replacement for treating an intervertebral disc. A barrier sealant membrane is deposited on a tissue surface within a denucleated space within an intervertebral disc. This is filled with a prosthetic nucleus material.

United States Patent Application 20050149191 by Cragg et al. published Jul. 7, 2005 shows a spinal mobility preservation apparatus with a proximal body, an intermediate body, a distal body, and an expandable membrane. The expandable membrane extends into the intervertebral disc space to support the spinal motion segment.

United States Patent Application 20040186576 by Biscup et al. (SpineCo.) published Sep. 23, 2004 shows a prosthetic implant for forming a support structure between adjoining vertebrae in a spinal column. The prosthetic implant includes a generally spherical or ellipsoidal body that at least partially engages a surface of adjacent vertebrae.

United States Patent Application 20030055506 by Stoy et al. published Mar. 20, 2003 shows a hydrogel-based prosthetic device for replacing at least a part of the nucleus of a spinal disc. The prosthetic device is composed of at least two essentially parallel soft layers of an elastically deformable hydrogel and at least one rigid layer, the rigid layer having less compressibility than the soft layers, being adjacent to the soft layers, parallel to them, and firmly attached to them.

U.S. Pat. No. 7,128,746 to Singer et al. (PMT Corporation) issued Oct. 31, 2006 shows a method and device for treating human intervertebral disc herniations using an endoscopic procedure. An access port is opened into and through the annulus of a disc to remove nucleus pulposus. A balloon device having a valve structure is positioned via an endoscopic procedure into the disc space, and the balloon device is filled with a physiological fluid to occupy the disc interspace or to maintain some degree of distraction of the created disc space.

U.S. Pat. No. 7,066,960 to Dickman issued Jun. 27, 2006 shows an intervertebral disk prosthesis formed of a matrix of bioincorporable fabric impregnated with a nuclear core mixed into the matrix and hardened. The core is a polymer, preferably of liquid form that cures into a viscoelastic solid, in which each component—polymer and fabric—reinforces the other against tearing, shearing and weakening under stress. Each edge of the outer fabric that interfaces a vertebral end plate is impregnated with an agent to stimulate osseus incorporation and anchoring.

United States Patent Application 20030033017 by Lotz et al. (Univ. of California) published Feb. 13, 2003 shows a nucleus implant for repairing degenerated intervertebral discs that is inflated inside the nucleus space after the degenerated nucleus has been removed to re-pressurize the nuclear space within the intervertebral disc. The implant is inflated with a high molecular weight fluid, gel or combination of fluid and elastomer, through a self-sealing valve that allows one-way filling of the implant after it is placed within the disc.

Finally, United States Patent Application 20050033437 by Bao et al. (Pioneer Laboratories, Inc.) published Feb. 10, 2005 shows an artificial disc device for replacing a damaged nucleus. The device may be inserted into the natural annulus in a collapsed or compressed state or arrangement and then be expanded. Many variations are shown, one (FIG. 34) including opposing spacer plates coupled together at a canister 220 with telescoping walls. The canister may be filled with fluid, or may be filled with elastomeric material, or a balloon.

However, none of the preceding inventions presents an ideal replacement for the natural intervertebral disc is supplants. An ideal replacement would mimic the properties of the natural disc by maintaining the intervertebral disc space through a full range of natural motion, absorb the shocks of daily use, permit a natural range of motion and yet resist hyper extension of the joint, limit wear so as to extend the useful life of the implant, be collapsible or compressible so as to be implantable through minimally invasive techniques and be simple to manufacture and assemble.

SUMMARY OF THE INVENTION

Accordingly, it is an object of the invention to provide an artificial disc prosthesis that mimics the properties of the natural disc by maintaining the intervertebral disc space through a full range of natural motion, absorbs the shocks of daily use, permits a natural range of motion and yet resists hyper extension of the joint, limits wear so as to extend its useful life, is collapsible or compressible so as to be implantable through minimally invasive techniques and is simple to manufacture and assemble.

In accordance with one aspect of the present invention, a multi-piece disc replacement implant device is disclosed for replacing a disc removed by a discectomy. The implant includes an upper plate member, a lower plate member, and an intermediate resilient member implant providing movement between the two plate members replicating the natural movement of the spine including flexion/extension, lateral bending, and, in some embodiments, rotation. Each of the plate members are generally formed to be rigid. The resilient member is an elastic solid or a multi-chamber balloon structure of fluid-filled sacks that collectively define a non-uniform shape such as an oblate spheroid, or a helically coiled string of beads. Such an implant is capable of supporting the compressive and cyclic loads required of a natural disc. The upper and lower plate members are cooperatively formed to selectively limit the allowable range of motion in any given direction.

The various embodiments of the present invention may be implanted by anterior, anterio-lateral, or posterior surgical approach. The size of each implant component (in collapsed form) is small enough that they may be inserted with minimal incisions. Furthermore, the implant components can be inserted through the posterior of the spine. A posterior approach to the surgical site reduces the invasiveness of the procedure and may often be performed by a single orthopedic surgeon or neurosurgeon without a need for a general surgeon which substantially decreases the cost and complexity of the procedure.

BRIEF DESCRIPTION OF THE DRAWINGS

Other objects, features, and advantages of the present invention will become more apparent from the following detailed description of the preferred embodiment and certain modifications thereof, in which:

FIG. 4 is a perspective view of the multi-chamber balloon included within the prosthesis of FIGS. 1-3.

FIG. 5A is a perspective view of an alternate embodiment of the multi-chamber balloon having a double toroid shape.

FIG. 5B is a side view of an alternate embodiment of a multi-chamber balloon having a double toroid shape.

FIG. 5C is a top view of an alternate embodiment of a multi-chamber balloon having a double toroid shape.

FIG. 5D is a top view of an alternate embodiment of a multi-chamber balloon having a double toroid shape.

FIG. 5E is a top view of an alternate embodiment of a multi-chamber balloon having a double toroid shape.

FIGS. 9A and 9B are opposing perspective views of an upper plate member according to an embodiment of the invention.

FIGS. 10A and 10B are opposing perspective views of a lower plate member according to an embodiment of the invention.

FIG. 11 is a perspective view of an artificial disc prosthesis according to an embodiment of the invention.

FIG. 12A is a side view of an artificial disc prosthesis according to an embodiment of the invention.

FIG. 12B is a top view of an artificial disc prosthesis according to an embodiment of the invention.

FIG. 12C is a section through an artificial disc prosthesis according to an embodiment of the invention.

FIG. 12D is an anterior view of an artificial disc prosthesis according to an embodiment of the invention.

DETAILED DESCRIPTION OF THE PREFERRED EMBODIMENTS

The present invention comprises intervertebral disc implants incorporating single or multi-chamber balloons of varying shape that inflate to a unified whole of various forms including regular and irregular oblate spheroids and coiled strings of balloons, any of which may be implanted in an anterior, anterior-lateral, or a posterior surgical procedure with minimal incisions.

Figure 1:
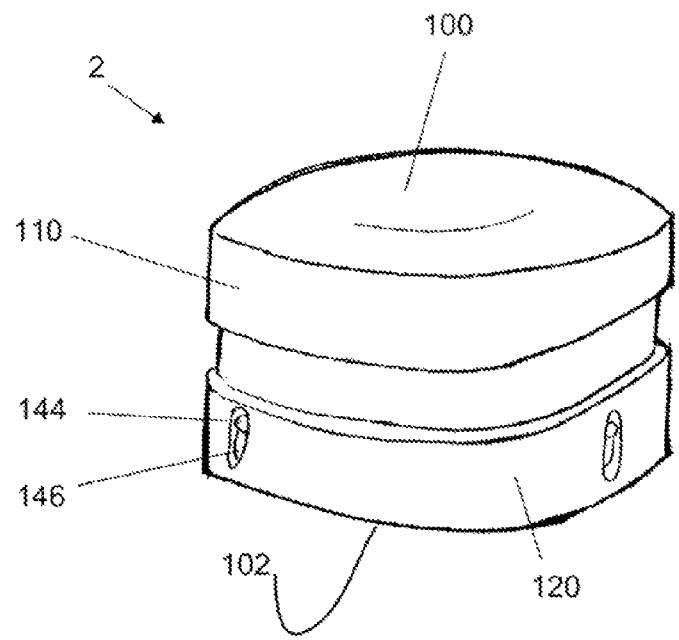
FIG. 1 is a perspective view of an artificial disc prosthesis according to a first embodiment of the present invention.
Figure 2:
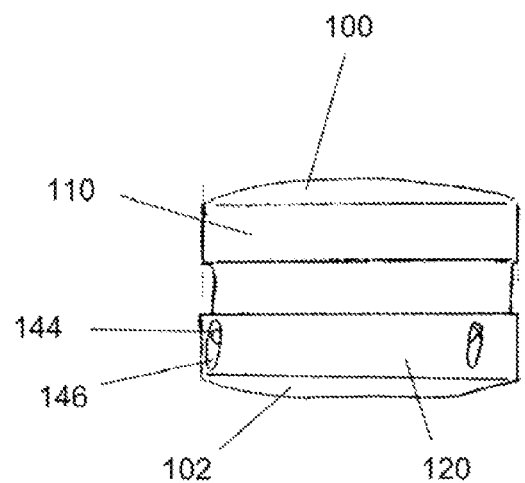
FIG. 2 is a side view of the disc implant 2 of FIG. 1.

FIG. 1 is a perspective view of the intervertebral disc implant 2 according to a first embodiment of the present invention. FIG. 2 is a side view of the disc implant 2 of FIG. 1 and FIG. 3 is a cross sectional view of the disc implant 2 of FIG. 1. With combined reference to FIGS. 1, 2 and 3, a first embodiment of the present invention incorporates an upper, or superior, plate member 100, and a lower, or inferior, plate member 102, which are adapted to be secured to upper and lower vertebra, respectively, in a spinal column. A single or multi-component resilient member 103 (FIG. 3) is also provided, disposed between the upper and lower plate members 100, 102. It is to be noted that the reference to the plate members as upper and lower members is for the purpose of identifying these members in the drawings. It may well be possible that the positions of the two plate members are be reversed.

Each of the upper and lower plate members 100, 102 is provided with means for securement to the upper and lower vertebra (not shown) including the use of screws through the plate members and into the vertebral body or through tabs affixed to the plate members and into the vertebral body. Also described is the use of posts, spikes or fins affixed to the top and bottoms surfaces of the plate members for engagement with cooperative holes or slots prepared in the adjacent vertebral body. Plate members 100, 102 may further have their bone-contacting surfaces manufactured and/or treated or modified to facilitate or improve bonding to the bone. Several such approaches are known in the art and should be suitable for use with the present invention.

Upper and lower plate members 100, 102 are respectively provided with interfitted (telescoping) sidewalls 110, 120 extending inward (toward one another) from the opposing surfaces of the plate members to form a housing for seating and containing the resilient member 103. The sidewalls 110, 120 are of sufficient height to overlap one another when the balloon or resilient member 103 is fully expanded after implantation. One or both of the sidewalls 110, 120 may be formed with a thicker portion 112 proximal to the plate from which is extends and a thinner distal end 114 for overlapping with the opposing sidewall. The transition from the proximal portion 112 to the distal portion 114 provides a positive stop 116 against which the distal end of the opposing sidewall my rest. The positive stop 116 provides a maximum limit that the intervertebral disc implant 2 may articulate in a particular direction as a result of compression of the inner resilient member 103.

Figure 6:
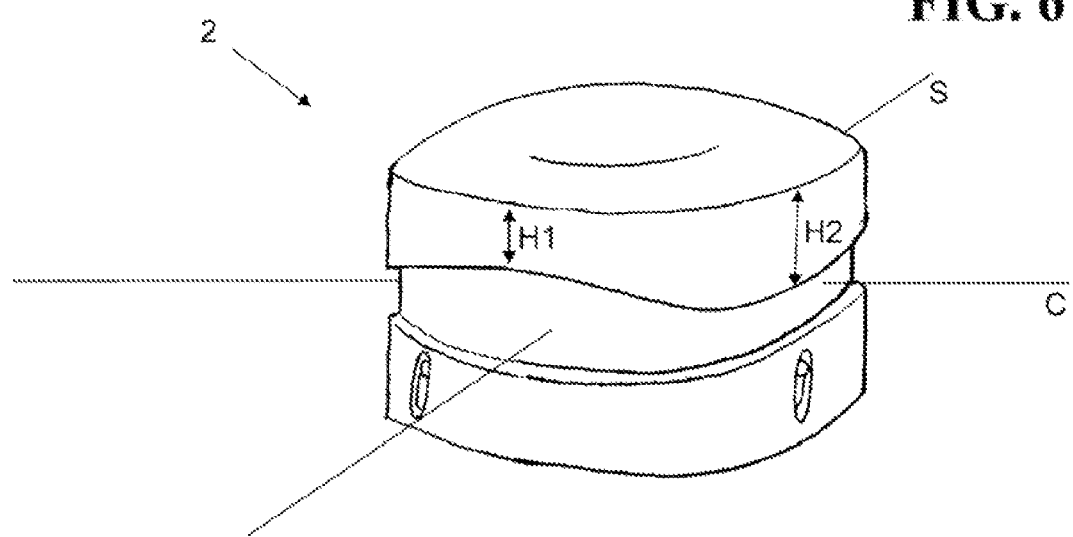
FIG. 6 is a perspective view of an alternate embodiment of the intervertebral disc implant.
Figure 7:
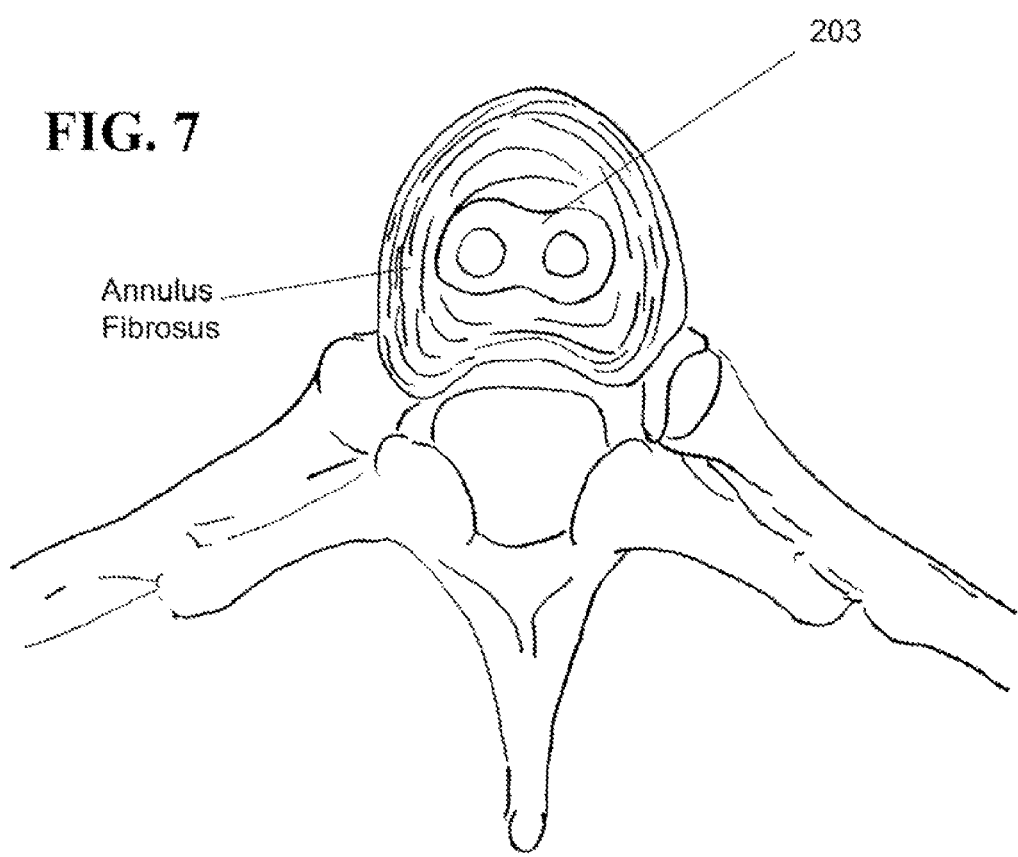
FIG. 7 is a top sectional view of the intervertebral disc prosthetic in-situ.

The maximum limit provided by the positive stop 116 may be the same in all directions as depicted in the embodiment of FIG. 1. Alternately, the height of the proximal portion 112 may be varied about the circumference of the intervertebral disc implant 2 as depicted in FIG. 6 to permit relatively more articulation in, for example, the sagital plane (S) than in the coronal plane (C). The height of the proximal portion setting the position of the positive stop 116 in the sagital plane (H2) is less than the height of the proximal portion setting the position of the positive stop 116 in the coronal plane (H1) such that greater movement of the upper and lower plate members 100, 102 is permitted. Such variation in height of the proximal portion 112 is preferable done through a continuous curve and may permit greater motion in one direction of a given plane than in another direction (i.e. bending forward is permitted while bending backwards is not).

Figure 3A:
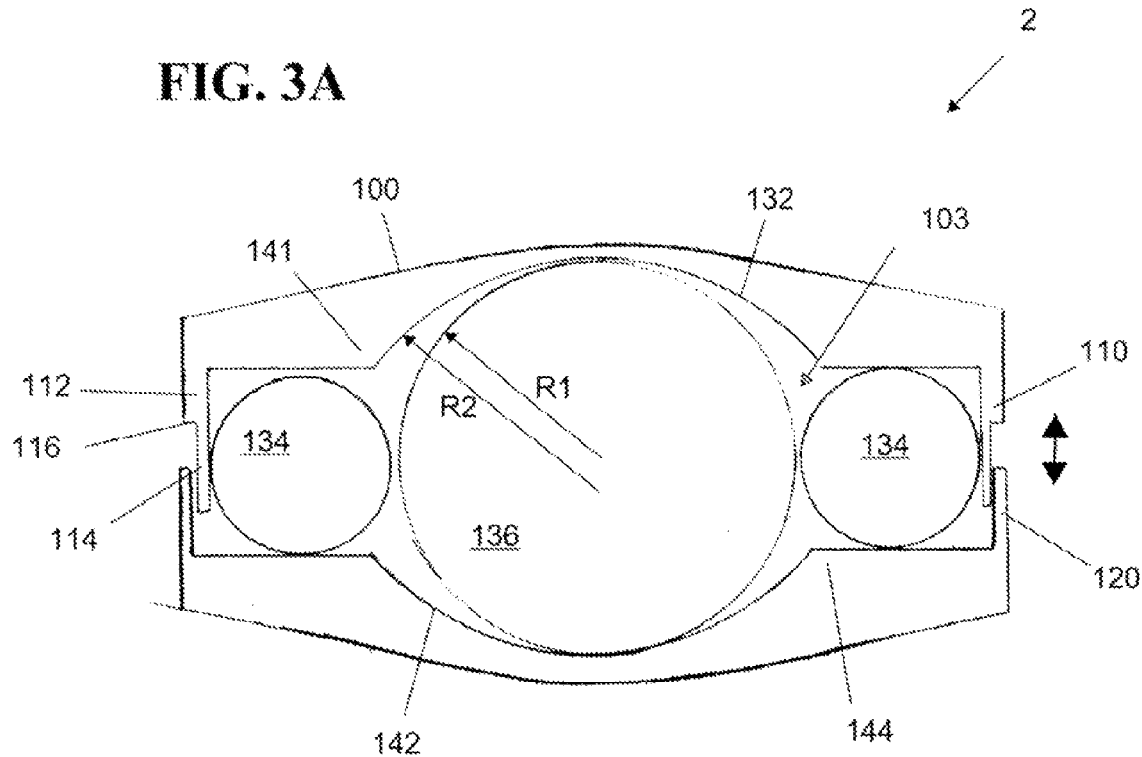
FIG. 3A is a side cross-section of the artificial disc prosthesis according to a first embodiment of the present invention.
Figure 3B:
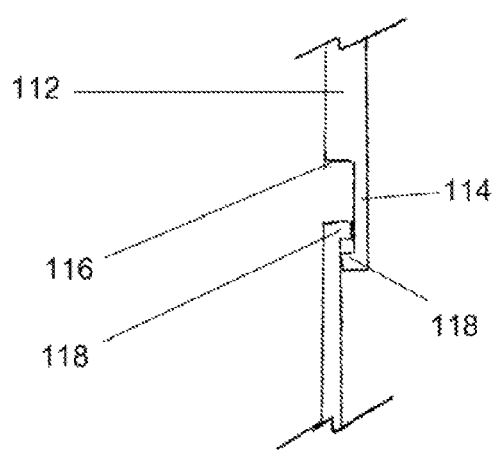
FIG. 3B is a detail side cross-section of an alternate embodiment of the sidewalls having annular rings at their distal ends so as to interlocking

Sidewalls 110, 120 may be formed with annular rings 118 at their distal ends as depicted in FIG. 3b so as to be interlocking thereby preventing the upper and lower plate members from separating during articulation of the spine. As described above with respect to the positive stop 113, the position of the rings may be varied about the circumference intervertebral disc implant 2 to permit relatively more articulation in one plane or direction over another. It should be observed that while the depicted embodiment shows the lower sidewall extending outside and over the distal end of the upper sidewall the intervertebral disc implant 2 could be constructed such that the distal end of the upper sidewall extends outside and over the lower sidewall with similar efficacy.

Sidewalls 110, 120 may also be formed, as depicted in FIGS. 1 and 2 with a radial sequence of protruding guides 144 (two are shown) formed in the outer surface of the distal end of sidewall 110. Guides 144 are captured within vertical slots 146 in the sidewalls 120 of the opposing plate 102. The protruding guides 144 slide along the vertical slots 146 and prevent relative rotation of the plates 100, 102, but permit a limited degree of pivoting flexion. Slots 146 and guides 144 may be utilized in conjunction with or in place of annular rings 118 to also prevent separation of the upper and lower plate members 100, 102 during articulation and to control the limits thereof. Variation in the length of the slots 146 is used to control the limits of articulation. In a preferred embodiment four slot 146 and guide 144 pairs are implemented, one each at the cardinal points about the intervertebral disc implant 2 although more or less, including zero slots/guides may be used. Additionally, walls 110, 120 may be formed with a predetermined coefficient of friction on the overlapping portions in order to augment the resilient member 103 in controlling or restricting movement between the upper plate 100 and lower plate 102.

With reference to FIG. 3A, the upper plate member 100 preferably has a lower surface formed with a concave impression 132 that is complementary to the shape of the resilient member 103. The lower plate member 102 is likewise preferably formed with a lower surface having a concave impression 142 that is similarly complementary to the shape of the resilient member. In a preferred embodiment upper and lower plate members 100, 102 are circular in plan such that the space enclosed by the intervertebral disc implant 2 is substantially cylindrical although other forms are contemplated as described below. The space enclosed by intervertebral disc implant 2 is occupied by a resilient member 103 as depicted in FIG. 4.

Resilient member 103 is formed with a generally toroidal member 134 (i.e. doughnut shaped) encircling a spherical member 136 that fits within a central aperture of the toroidal member 134. The entire member 103 (including both members 134 and 136) may be formed as an integral component or as two discrete components that are fitted together as suggested by FIG. 3A. The resilient member 103 may be made of any of a variety of known biocompatible resilient compounds such as silicone rubbers, polyether and polyester urethane, polymethyl methacrylate, polycarbonates and various other polymerizing resins or hydrogels having the desired elastic properties. Further, the individual members 134, 136 may each be selected from an elastomer having different elastic properties to achieve the desired operation of the intervertebral disc implant 2 as described blow.

In a preferred embodiment resilient member 103 is formed as a multi-chamber balloon having a toroidal chamber 134 encircling a spherical chamber 136. Both chambers 134, 136 are defined by expandable side walls made, for example, of silicone rubber. Both chambers 134, 136 may be inflated either before, or preferably, after implantation. In combination the inflated chambers of balloon 103 define an oblate spheroid shape which approximates the shape of the disc it is meant to replace. The chambers may be inflated with air (or another gas) or with any of a variety of liquid or viscous substances as well as curing resins to achieve the desired elastic properties as described. Further, the toroidal chamber 134 and the spherical chamber 136 may each be inflated with different substances to achieve the desired operation.

With reference to FIGS. 9-12, an alternate embodiment of the present invention is disclosed having an upper plate member 100 and lower plate member 102 having a generally rounded rectangular shape in plan view. The sidewalls 110 of the upper plate member 100 extend down and receive the upwardly extending sidewalls 120 of the lower plate member to define an internal void in which the resilient member(s) will be seated. The anterior sidewalls of both the upper and lower plate members are each provided with an opening 90, preferably semi-circular, such that the assembled implant 2 is provided with an aperture 91 through its anterior face to permit access to the internal void and to the resilient member 103 during surgical implantation. The lateral sidewalls of the upper plate member 100 are provided with a shallow recess 216 on their inner surface while the lateral sidewalls of the lower plate member 110 are provided with a protruding ridge 218 for cooperative engagement with the recess 216 to limit the relative movement of the upper and lower plate members and prevent the upper and lower plate members from separating during articulation of the spine.

In order to secure the prosthesis 102 within the intervertebral space, a bore or aperture 304 is provided through each of the upper and lower members 100, 102 joining their outer surfaces with the internal void in order to allow a bone screw 300 to be driven through the plate and into the bone of the adjacent vertebrae from within the void. A boss or post 301 is preferably provided encircling the aperture 304 to reinforce the opening and permit the inner surfaces of the upper and lower plate members to be formed with a countersink or counter-bore in order to recess the bone screw head so as not to engage the resilient member 103 in-situ. The post 301 may also be provided separate and apart from the aperture 304. During a surgical procedure to implant a prosthetic of this embodiment, a channel is bored or cut into the surface of the adjacent superior or inferior vertebral body extending from the anterior face of the bone. The post 301 is received in the channel as the prosthetic is slid into the intervertebral space vacated by the disc. Seating of the post 301 in such a channel resists lateral or posterior translations of the device under the loads experienced during the daily activities of the patient. A secondary post 302 may be provided extending from the upper and lower surfaces of the upper and lower plate members, respectively, at the anterior edge of the prosthesis. The secondary post 302, if present, is also received within the bored or cut channel in the bone and serves to resist both lateral translation and rotation of the implant during daily use.

In use the resilient member is compressed within the intervertebral disc implant 2 by a retaining clip or similar so as to present a smaller overall height to ease insertion into the evacuated intervertebral space. After insertion the clip is removed to permit the resilient member to expand and the implant to return to its operative dimensions. Where the resilient member is a balloon, the implant may be inserted with the balloon deflated, the chambers being inflated after the device is positioned. Inflation may be accomplished by insertion of a syringe (not shown) through a port 119 in the surface of each chamber so as to inject a fluid or resin filler. Where one or more bone screws are to be used through the upper and/or lower members 100, 102, the balloon may inserted via aperture 91 and inflated after the prosthetic 2 is implanted and secured in place The spherical member 136 when inflated seats itself within the opposing concave impressions 132, 142, in the upper plate member 100 and lower plate member 102, respectively. In a preferred embodiment impressions 132, 142 are formed with a slightly greater radius (R2) than the spherical member 136 to afford a limited degree of pivoting freedom for flexation. This way, the upper vertebrae may shift either laterally or in a front or rearward direction, relative to the lower vertebrae. This flexion is facilitated by the interfitted (telescoping) sidewalls 110, 120 extending inward from the major surface of the plates 100, 102. The telescoping sidewalls 110, 120 are free to slide together/apart as described. Certain embodiments may include one of only an upper or lower concave impression 132, 134.

The spherical member 136 acts a shock absorbing member with the shock absorbing ability a function of by the elastic properties of the chosen elastomer or balloon material and filler. As the spine is articulated, for example rotated forward in the sagital plane during daily activity the shoulders 141, 144 of the upper and lower plate members 100, 102 formed about the periphery of the concave impressions 132, 142, or the periphery itself, engages the surface of the torroidal chamber 134. The elastic properties of the chosen elastomer or balloon material and filler of the torroidal chamber 134 determine the resistance of the implant 2 to this flexion. By choosing the relative and absolute elastic properties of the two resilient members the surgeon may customize the operational characteristics of the implant as both a shock absorber and an articulating joint to match the natural properties of patients original intervertebral disc and meet the needs of the patient.

FIG. 5A is a perspective view of an alternative embodiment of a resilient member 203. FIG. 5B is a side view and FIG. 5C is a top view of this alternate embodiment. The resilient member 203 is formed with a double toroid member 236, here encircling two spaced spherical chambers 234, 238 that fit within spaced central apertures of the toroidal chamber 236. While the term double torroid is used to describe the encircling member, it should be observed that the form need not be precisely a double torroid in the mathematical sense. Rather, double torroid is herein defined to include the join of two closed loops in the same plane which may ultimately be an ellipse (FIG. 5D), ovoid or rounded rectangle (FIG. 5E) in plan view.

Figure 8:
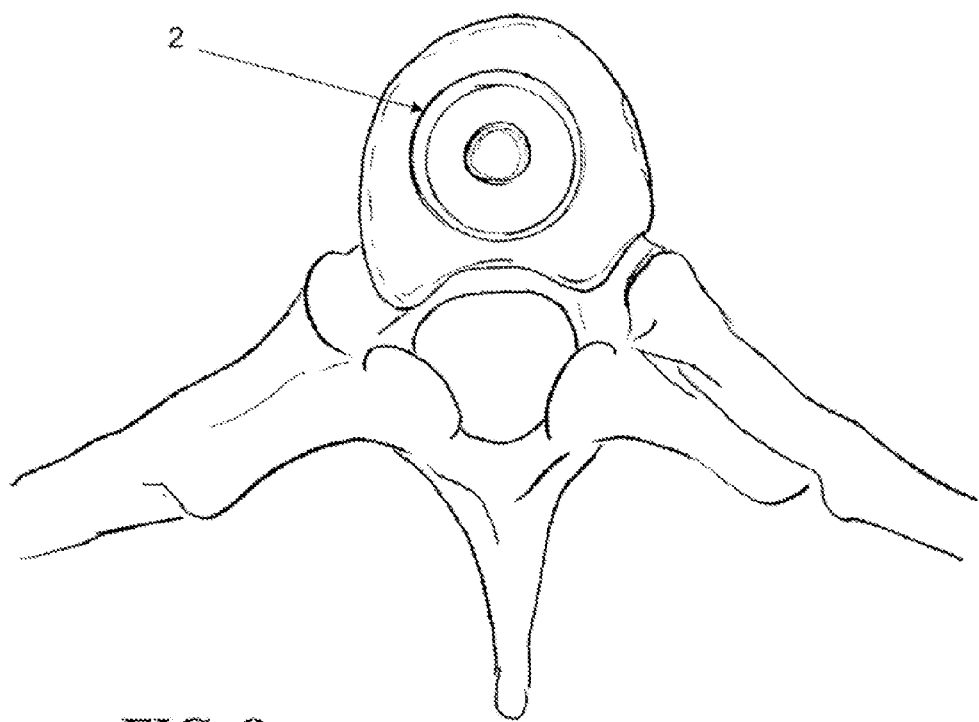
FIG. 8 is a top sectional view of an alternate embodiment of the intervertebral disc prosthetic in-situ.
Figure 13:
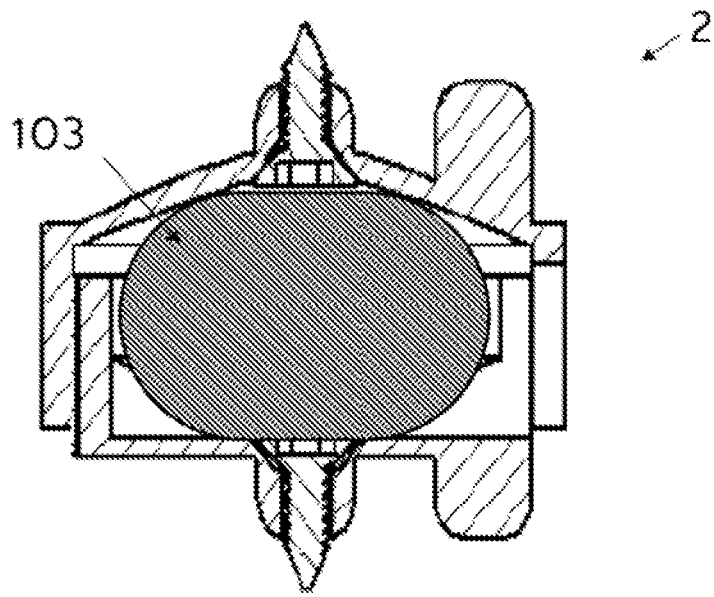
FIG. 13 is a section view through an artificial disc prosthesis according to an embodiment of the invention.
Figure 14:
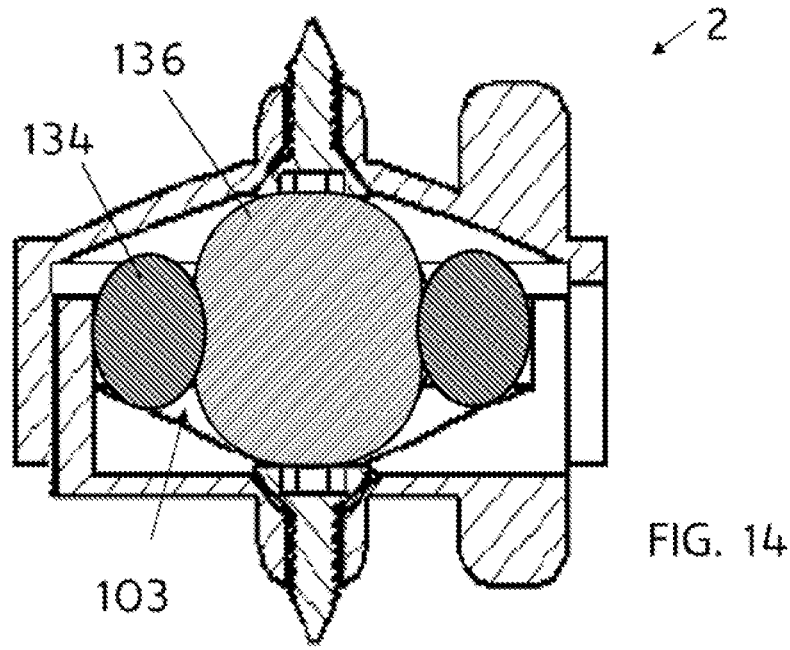
FIG. 14 is a section view through an artificial disc prosthesis according to an embodiment of the invention.

As above, the resilient member 203 may be a balloon wherein the spherical chambers may be integrally formed components with the torroidal chamber 236 or each may be formed as a discrete component that is fitted together. The balloon members are constructed from similar materials and in a similar manner as the multi chamber balloon of the first embodiment of the present invention. The overall shape of the intervertebral disc implant 2 would, of course, no longer be cylindrical but rather would accommodate the form of resilient member 203. It should be observed that intervertebral disc implant 2, when formed to accommodate resilient member 203, will have a major and minor axis whereas the first embodiment, being roughly cylindrical, was symmetrical about any axis. Spherical chambers 234, 238, being arranged along the major axis provide relatively more resistance to articulation and flexion about the minor axis such that the surgeon may selectively implant the device with the axis oriented to further provide variable resistance to articulation in one plane over another. FIG. 8 depicts the device implanted in the interdiscal space with the major axis oriented in the coronal plane such that rotation in the sagital plane (i.e. medial/dorsal bending) is relatively easier than lateral bending.

Figure 15:
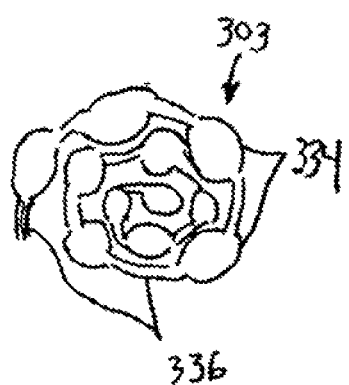
FIG. 15 is a top perspective view of another alternative embodiment of a multi-chamber balloon coiled into a helix.

FIG. 15 is a top perspective view of another alternative embodiment of a multi-chamber balloon 303 coiled into a helix. The balloon 303 is here formed with a plurality of spaced spherical chambers 334 connected by capillary conduits 336 and resembling a string of Christmas lights or beads. In this case the entire balloon 303 (all chambers 334 and conduits 336) are preferably formed as an integral component from, for example, silicone rubber. The interior of all chambers 334 and conduits 336 remain in fluid communication so that all chambers 334 may be inflated simultaneously via an end conduit 336 having a self sealing port 19. Multi balloon chamber 303 may be incorporated into an intervertebral disc implant 2 in place of the resilient members 103 or 203. Alternately, where the nucleus pulpous has been evacuated from the intervertebral disc by the surgeon or otherwise dissipated due to time or injury but the annulus fibrosus remains substantially intact, the balloon 303 may be inserted directly into the void through an incision or break in the annulus fibrosus. Once in place it may be inflated to replace the lost nucleus pulpous. In yet another alternate embodiment a similar procedure may be performed utilizing a balloon resilient member 203 such that the resilient member is inserted with the annulus fibrosus and inflated absent an intervertebral disc implant 2.

In each of the foregoing embodiments, the balloons 103, 203 may be inserted in a deflated state, and later inflated by hypodermic or other inflation pump to define their respective shapes. One skilled in the art should now understand that any variety of desired shapes my be established with the basic multi-chamber balloon concept, and such variations are considered to be within the scope and spirit of the present invention. Once inflated, the implants 103, 203 are capable of supporting the compressive and cyclic loads required of a natural disc. The size of each implant component (in collapsed form) is small enough that they may be inserted with minimal incisions. Furthermore, the implant components can be inserted through the posterior of the spine. A posterior approach to the surgical site reduces the invasiveness of the procedure, and may often be performed by a single orthopedic surgeon or neurosurgeon without a need for a general surgeon, and thus substantially decreases the cost and complexity of the procedure.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

I claim:

1. An implantable prosthetic for replacing an intervertebral disc of a spinal column, said implantable prosthetic comprising:
    a housing enclosing a void, said housing further comprising
        a monolithic upper housing member having a first upper surface adapted for cooperative engagement with a superior vertebra and a first lower surface opposite to said first upper surface, a first sidewall extending downwardly from a first peripheral edge of said first lower surface and surrounding the void, a first post extending from a center of said first upper surface longitudinally in a first direction away from the first upper surface and away from the void, said first post configured for insertion within a first channel prepared in said superior vertebra, a second post at said first peripheral edge extending in a second direction away from said first upper surface and from the void parallel to the first direction, said second post configured for engagement within said first channel prepared in said superior vertebra, and a first bore extending from said void through said upper housing member and longitudinally through said first post for receiving a bone screw configured to be driven into said superior vertebra,
        a monolithic lower housing member having a second lower surface adapted for cooperative engagement with an inferior vertebra and a second upper surface opposite to said second lower surface, a second sidewall extending upwardly from a second peripheral edge of said second upper surface and surrounding the void, a third post extending from a center of said second lower surface longitudinally in a third direction away from the lower surface and away from the void, said third post configured for insertion within a second channel prepared in said inferior vertebra, and a second bore extending from said void through said lower housing member for receiving a bone screw configured to be driven into said inferior vertebra, said first sidewall of said upper housing member slideably engaged with said second sidewall of said lower housing member to define said void, a resilient member seated in said void, said resilient member engaging said first lower surface of said upper housing member and said second upper surface of said lower housing member so as to replicate the natural relative movement of the superior and inferior vertebra;

a first bone screw through and out from said first bore of said upper housing member and configured to extend into said superior vertebra; and a second bone screw through and out from said second bore of said lower housing member and configured to extend into said inferior vertebra.

2. The prosthetic device of claim 1, wherein said second post is aligned with said first post along an anterior-posterior axis of said upper housing member.

3. The prosthetic device of claim 1, wherein said lower housing member further comprises a fourth post at said second peripheral edge and extending in a fourth direction away from said lower surface and from the void parallel to the third direction, said fourth post configured for engagement within said second channel prepared in said inferior vertebra.

4. The prosthetic device of claim 3, wherein said fourth post is aligned with said third post along an anterior-posterior axis of said lower housing member.

5. The prosthetic device of claim 1, wherein said resilient member is further comprised of a plurality of resilient sub-members.

6. The prosthetic device of claim 1, wherein said resilient member comprises a balloon.

7. The prosthetic device of claim 6, wherein said resilient member comprises a balloon having a plurality of inflatable chambers.

8. The prosthetic device of claim 7, wherein said plurality of inflatable chambers comprised of a first inflatable chamber having a substantially toroidal shape and a second inflatable chamber having a substantially spherical shape, the second inflatable chamber occupying a central void of said toroidal first chamber.

9. The prosthetic device of claim 8, wherein at least one of said lower surface of the upper housing member and said upper surface of said lower housing member is formed with a recess substantially in the shape of a spherical segment, said recesses engaged by the surface of the spherical second inflatable chamber.

10. The prosthetic device of claim 9, wherein said spherical second inflatable chamber is sized to be seated within said recesses.

11. The prosthetic device of claim 7, wherein said plurality of inflatable chambers comprised of a first port for inflating a first inflatable chamber and second port for inflating a second inflatable chamber.

12. The prosthetic device of claim 7, wherein said plurality of inflatable chambers comprised of a first inflatable chamber having a double toroid shape, a second inflatable chamber having a spherical shape and a third inflatable chamber having a spherical shape, the second inflatable chamber occupying a first central void of the first chamber and the third inflatable chamber occupying a second central void of the first chamber.

* * * * *